(12) United States Patent
Don Michael et al.

(10) Patent No.: US 6,485,502 B2
(45) Date of Patent: Nov. 26, 2002

(54) VASCULAR EMBOLISM PREVENTION DEVICE EMPLOYING FILTERS

(76) Inventors: T. Anthony Don Michael, 4109 Sill Pl., Bakersfield, CA (US) 93306; Peter Besselink, Gronausestratt 1220, 7534 AT Encschede (NL)

(*) Notice: Subject to any disclaimer, the term of this patent is extended or adjusted under 35 U.S.C. 154(b) by 0 days.

(21) Appl. No.: 09/803,641

(22) Filed: Mar. 12, 2001

(65) Prior Publication Data

US 2001/0044634 A1 Nov. 22, 2001

Related U.S. Application Data

(60) Provisional application No. 60/188,179, filed on Mar. 10, 2000.

(51) Int. Cl.$^7$ .............................................. A61M 29/00
(52) U.S. Cl. ...................................... 606/200; 606/159
(58) Field of Search ................................ 606/191, 200, 606/159, 198; 604/104, 105, 106, 107

(56) References Cited

U.S. PATENT DOCUMENTS

| | | | | |
|---|---|---|---|---|
| 4,425,908 A | * | 1/1984 | Simon | 128/899 |
| 4,619,246 A | * | 10/1986 | Molgaard-Nielsen et al. | 128/899 |
| 4,867,742 A | | 9/1989 | Calderon | |
| 4,911,163 A | | 3/1990 | Fina | |
| 5,108,419 A | | 4/1992 | Reger et al. | |
| 5,626,605 A | * | 5/1997 | Irie et al. | 606/200 |
| 5,833,644 A | | 11/1998 | Zadno-Azizi et al. | |
| 5,833,650 A | | 11/1998 | Imran | |
| 5,885,258 A | | 3/1999 | Sachdeva et al. | |
| 5,893,867 A | | 4/1999 | Bagaoisan et al. | |
| 5,997,562 A | | 12/1999 | Zadno-Azizi et al. | |
| 6,013,093 A | * | 1/2000 | Nott et al. | 606/200 |
| 6,022,336 A | | 2/2000 | Zadno-Azizi et al. | |
| 6,053,932 A | * | 4/2000 | Daniel et al. | 604/104 |
| 6,364,895 B1 | * | 4/2002 | Greenhalgh | 606/200 |

FOREIGN PATENT DOCUMENTS

| | | |
|---|---|---|
| DE | 41 01 935 | 7/1992 |
| WO | 99 16362 | 4/1999 |
| WO | 99 44542 | 9/1999 |
| WO | 01 08743 | 2/2001 |

\* cited by examiner

*Primary Examiner*—Danny Worrell
(74) *Attorney, Agent, or Firm*—Browdy and Neimark, P.L.L.C.

(57) ABSTRACT

A method and system for preventing embolism and optimizing flow to downstream organs in a blood flow circuit incident to performance of a treatment at a location in a blood vessel, by: introducing a first filter element into the blood vessel downstream of the location so that the first filter element obturates the blood vessel; performing the treatment; introducing a second filter element into the blood vessel upstream of the location so that the second filter element obturates the blood vessel; and, after the step of performing a treatment, bringing the first and second filter elements close to one another, radially collapsing the first and second filter elements and withdrawing the first and second filter elements from the blood vessel.

23 Claims, 11 Drawing Sheets

FIG. 3
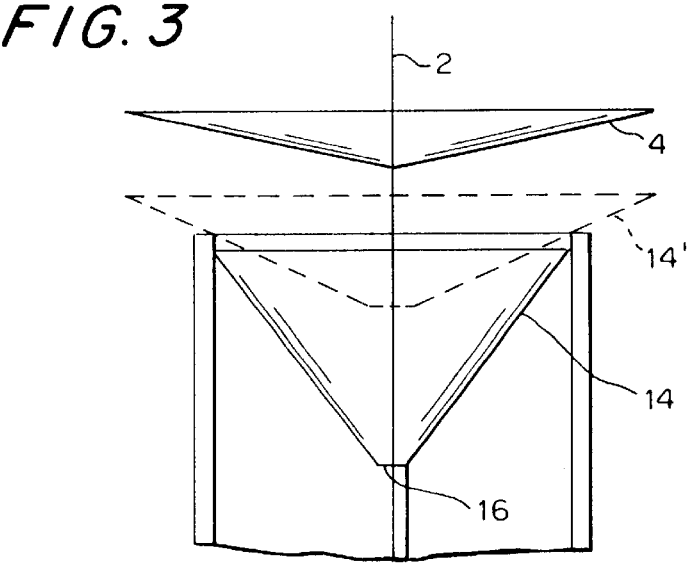
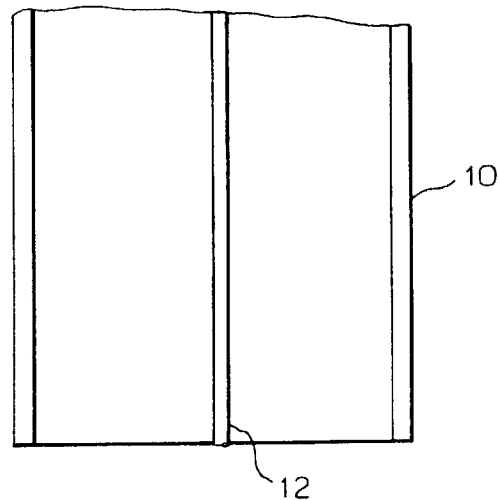
FIG. 4A
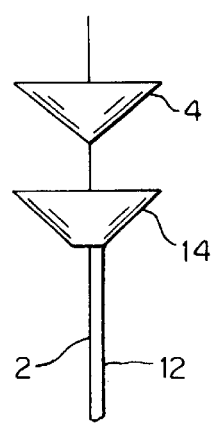
FIG. 4B
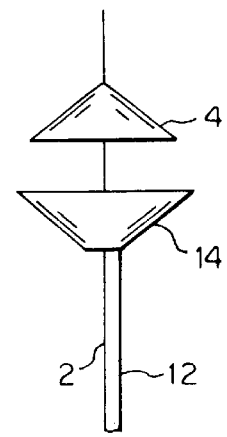

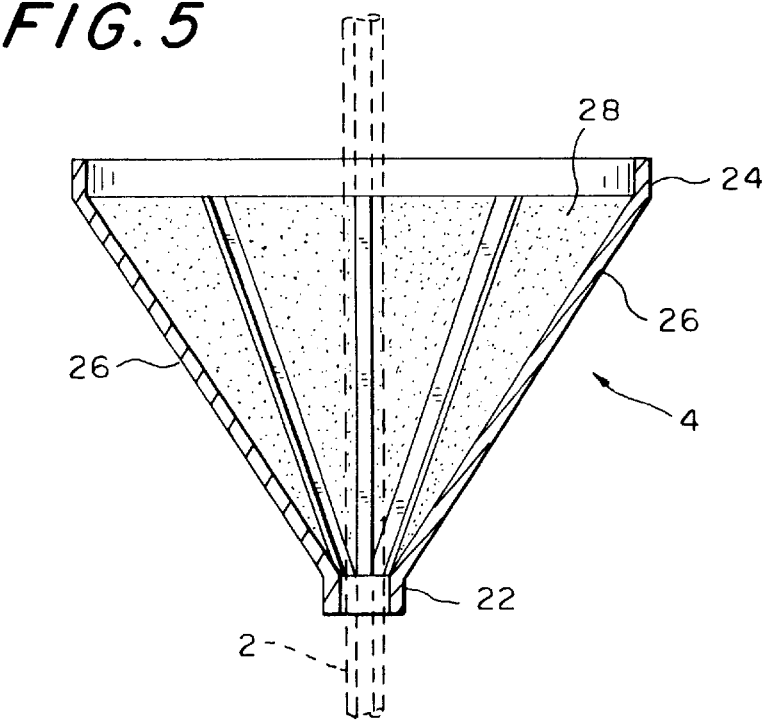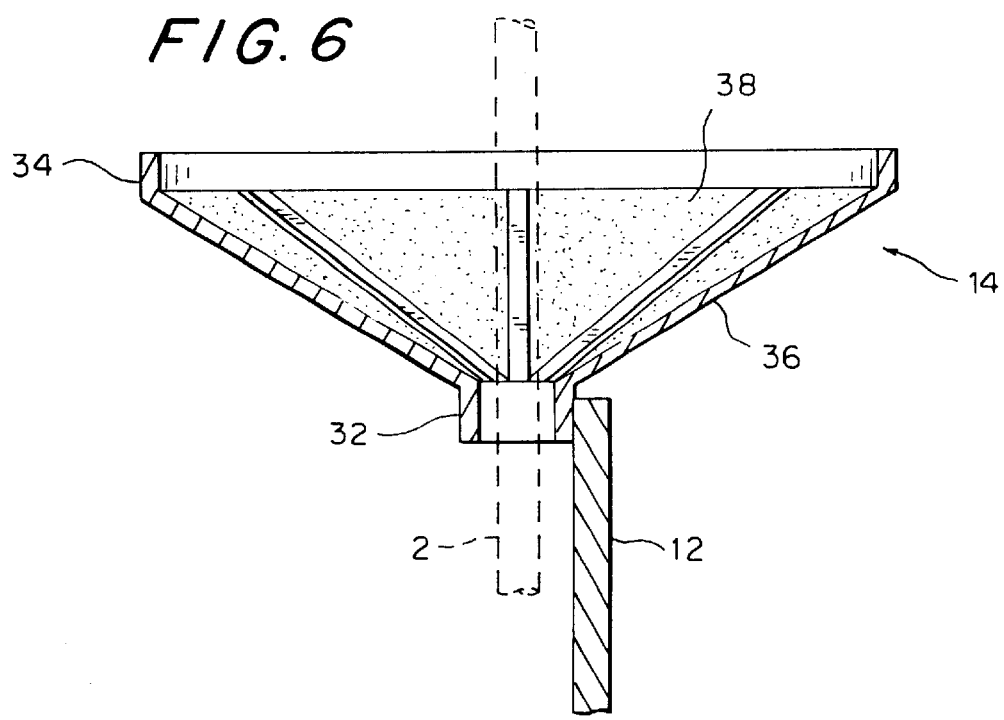

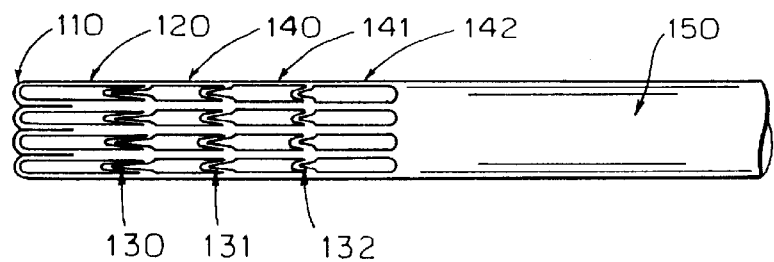
FIG. 12
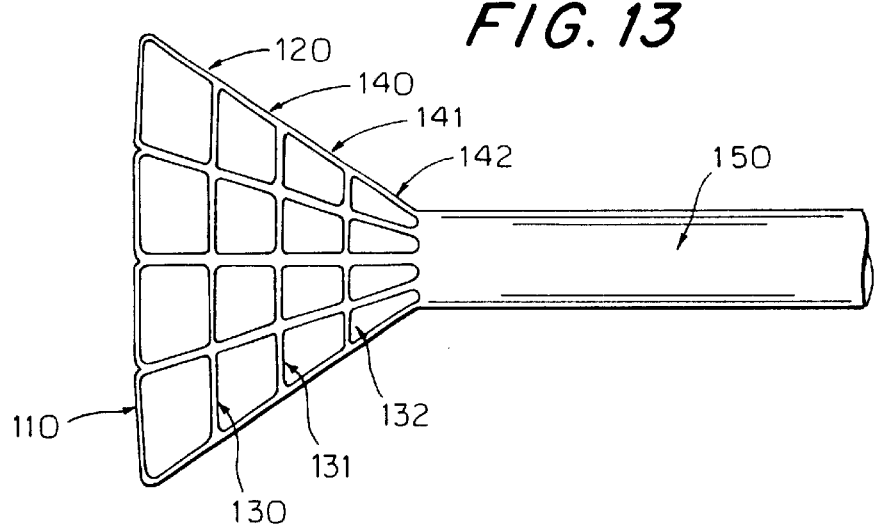
FIG. 13
FIG. 14
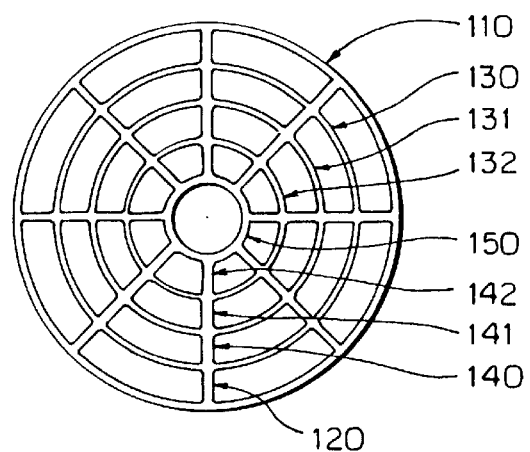

ial Application No. 60/188,179, filed Mar. 10, 2000.

VASCULAR EMBOLISM PREVENTION DEVICE EMPLOYING FILTERS

This application claims the benefit of the filing date of Provisional Application No. 60/188,179, filed Mar. 10, 2000.

BACKGROUND OF THE INVENTION

The present invention relates to medical procedures performed in blood vessels, particularly in arteries.

This invention relates more specifically to systems and methods involving angioplasty and/or stenting, where protection against loose embolic material is a major concern.

Such procedures are performed to remove obstructions or blockages in arteries and thereby alleviate life-threatening conditions. The procedures currently employed result in a fracturing or disintegration of the obstructing material and if the resulting particles, or debris, were permitted to flow downstream within the circulatory system, they would be likely to cause blockages in smaller arteries, or their microscopic branches termed the microcirculation, downstream of the treatment site. The result can be new life-threatening conditions, including stroke.

Various systems and techniques have already been proposed for removing this debris from the circulatory system in order to prevent the debris from causing any harm. These techniques involve temporarily obstruction the artery, at a location downstream of the obstruction, by means of an element such as a balloon, and then suctioning debris and blood from the treatment site. While such techniques can effectively solve the problem stated above, they require that blood flow through the artery be obstructed, causing complete cessation or at least a substantial reduction in blood flow volume, during a time period which can be significant for organ survival for example, the time limit for the brain is measured in seconds and for the heart, in minutes.

Although filters have been used, they suffer from the limitation of either obstructing flow or allowing micro embolism due to fixed pore size. Furthermore, the collected debris can reflux out of the filter when it is closed and lead to embolism. Upon pulling back of a basket/filter with entrapped particles into a delivery catheter, debris particles may be squeezed out of the device, because the volume is strongly reduced. During this pulling back, the filter no longer covers the full cross-section of the artery, so particles that are squeezed out then can freely flow around the outer edge of the filter and move distally through the artery.

The invention also relates to a combined delivery/post-dilatation device for self-expanding stents.

Normally the delivery of self-expanding stents is done with a separate delivery sheath, which is pulled back to release the compressed stent from this sheath and allow it to deploy. If this stent does not deploy to the full size, because the reaction forces of the artery wall and lesion site are too high, it must be further expanded by an additional post-dilatation procedure. Therefore, a separate post-dilatation catheter is needed, that has to be brought into the stented lesion site and then inflated to the full size. This is an extra, time-consuming step in the procedure.

BRIEF SUMMARY OF THE INVENTION

The present invention provides a method and device that prevent escape of debris from the treatment site in a blood vessel, and more specifically prevent embolism, by installing at least one appropriate filter with millipores specific to its use downstream, and possibly one such filter downstream of the treatment site in a blood vessel and manipulating those filters in a manner to assure that any debris created at the treatment site or refluxing from closure of the filters will be removed from the vascular system by physical withdrawal of the filters and/or suction.

For example, an embodiment of the invention may be a multistage, for example two filter, system composed of a first filter to filter the blood flow and a second filter to entrap debris from the first filter.

The invention further relates to a catheter system for delivery of a self-expanding stent with a combined function of delivery from a central sheath and post-dilatation, the system including a catheter having an inflatable outer section that surrounds the sheath at the distal end section of the catheter. The first step in a procedure using this system is the release of the stent by pushing it out of the sheath and pulling back of the catheter over a distance that is equal to at least the length of the stent. Then the catheter is advanced once more until the inflatable section is lined up with the stent again. For post-dilatation the inflatable section is inflated and the lesion plus stent are further expanded.

In one embodiment of the invention, the central lumen within the delivery sheath, where the stent has been pushed out, is reinforced to prevent it from collapsing by the hydraulic pressure of the post-dilatation balloon that surrounds it. Reinforcement of this sheath can be provided by giving the catheter a suitable rigidity at its distal end, for example by giving the catheter an increased thickness at that end. This may make the delivery sheath too rigid, which can be a disadvantage for use in tortuous arteries.

Therefore, the invention makes use of a more flexible delivery sheath that is prevented from collapsing by the use of a separate reinforcement. A pre-dilatation balloon can be lined up with the delivery sheath and inflated until it fills the lumen of this delivery sheath. In this way a concentric arrangement of two balloons, separately inflatable, gives a strong post-dilatation device that is extremely flexible in the deflated state.

A single common guide wire is used to bring the catheters to the lesion site, and the pre-dilatation catheter acts as a guiding means for the stent delivery sheath/post-dilatation balloon. By removal of the pre-dilatation catheter, leaving the inflated delivery catheter in place, a proximal occlusion system is created with a large working channel (the delivery sheath). In combination with a distal occlusion means, e.g. a distal balloon, a closed chamber is created in the artery and this can be reached with a range of instruments for inspection, treatment and flushing/suction purposes.

BRIEF DESCRIPTION OF THE DRAWING

FIG. 3 is view similar to that of FIG. 1 showing the first component and a second component of a system according to the invention.

FIGS. 4A and 4B are simplified pictorial views showing two basic embodiments of the invention.

FIGS. 5, 6 and 7A are cross-sectional elevational views of various alternative embodiments of filter components of a system according to the invention.

FIG. 12 is a side elevational view of a component of another embodiment of a system according to the invention, including a filter in its folded state.

FIG. 13 is a view similar to that of FIG. 12, showing the filter in its expanded sate.

FIG. 14 is an end view of the component with the filter in the expanded state.

FIG. 17 shows a guide wire brought into an artery with a lesion.

FIG. 18 shows a guiding catheter with a distal protection means, brought across the lesion over the guide wire.

FIG. 19 shows how the distal protection means is deployed until it reaches the artery walls.

FIG. 20 shows a predilatation catheter, which has been advanced over the guiding catheter, in its predilatation position with inflated balloon in the lesion section. Further FIG. 20 shows a delivery sheath with an inflatable distal section, holding a compressed stent, which is advanced over the predilatation balloon catheter.

FIG. 21 shows how the predilatation balloon is deflated and advanced across the lesion site, plus the semi-deployed stent after it has been delivered in the lesion area.

In FIG. 22 the two balloons are lined up and brought in the stent.

In FIG. 23 the predilatation balloon is inflated to create a support for the inflatable delivery sheath.

In FIG. 24 the inflatable delivery sheath is inflated to perform the final angioplasty and to reach full deployment of the stent.

In FIG. 25 the predilatation balloon catheter is removed from the patient's body while the inflated sheath is still in place.

In FIG. 26 the chamber in the artery between distal protection means and inflated sheath is flushed to remove or catch all debris.

In FIG. 27 the sheath is deflated and the distal protection means is collapsed, thus enabling removal from the artery, leaving only the stent in place.

DETAILED DESCRIPTION OF THE INVENTION

The invention provides a novel method and a system to confine and remove debris from a blood vessel, thereby preventing embolism in the vascular system.

A first step of one embodiment of a method according to the invention includes positioning a first particle filter in the blood vessel downstream of the treatment site.

Figure 1:
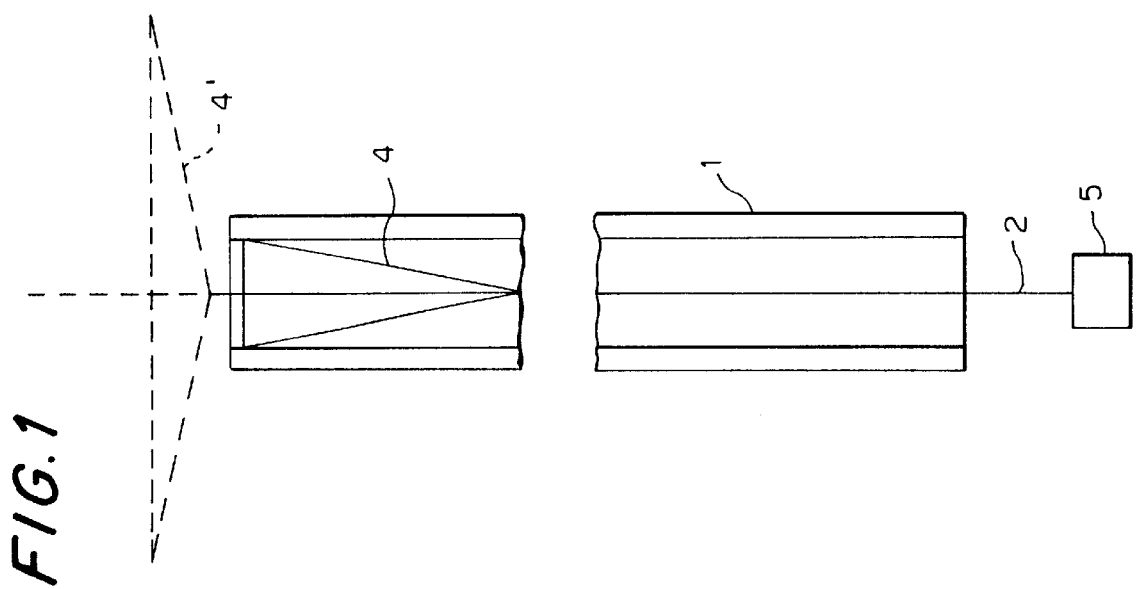
FIG. 1 is a simplified pictorial view illustrating a first component of a system according to the invention.

FIG. 1 is a cross-sectional elevational view of a first unit of a protective system according to the invention for carrying out the first step. This unit is composed of a sheath 1, a hollow guide wire 2 and a distal particle filter 4.

Filter 4 may have any shape, for example a conical shape, as shown, and is constructed to be radially expansible from a radially compressed state, shown in solid lines, to a radially expanded state, shown in broken lines at 4'. Preferably, at least one part of filter 4 is made of a resiliently deformable material that autonomously assumes the radially expanded state shown at 4' when unconstrained. Filter 4 may be shaped using appropriate shape setting procedures to open with a flared top portion made from highly elastic material such as the memory metal nitinol.

Sheath 1 serves to hold filter 4 in the radially compressed state during transport of filter 4 to and from the treatment site.

Filter 4 has a tip, or apex, that is fixed to guide wire 2. Guide wire 2 extends from a proximal end that will always be outside of the patient's body and accessible to the physician to a distal end that extends past the apex.

Guide wire 2 is preferably a hollow tube whose distal end is, according to the invention, used as a pressure sensor in communication with a pressure monitoring device 5 connected to the proximal end of guide wire 2. Device 5 is exposed to, and senses, via the longitudinal passage, or bore, in tube 2, the pressure adjacent to the distal end of guide wire 2.

Preferably, monitoring device 5 is removably fastened to the proximal end of guide wire 2. Device 5 would be removed, for example, when guide wire 2 is to be used to guide some other component of the device into the blood vessel after insertion of the first unit into a blood vessel, as will be described in greater detail below.

According to one practical embodiment of the invention, sheath 1 has an outside diameter of 1 to 1.5 mm and wire 2 has an outside diameter of 0.014–0.018 inch (approximately 0.5 mm) and is sized so that during insertion it will not disturb the obstruction that is to be removed. Filter 4 can be dimensioned to expand to an outer diameter of more than 1 mm, and preferably more than 10 mm. This dimension will be selected to be approximately as large as the diameter of the vessel to be treated.

Prior to insertion into a blood vessel filter 4 is arranged in sheath 1 as shown in FIG. 1. Then, in a conventional preliminary step, the blood vessel wall is punctured by a hollow needle, a preliminary guide wire (not shown) is introduced into the blood vessel through the needle, the needle is withdrawn, the opening in the blood vessel is dilated and a guiding catheter (not shown) is passed over the preliminary guide wire into the blood vessel to be treated. The distal, or leading, end of the guiding catheter is brought to an appropriate point ahead of an obstruction to be treated and the preliminary guide wire is withdrawn. Then, guide wire 2 and sheath 1, with filter 4 in place, are introduced into the blood vessel in the direction of blood flow, in a conventional manner through the guiding catheter, until filter 4 is at the desired location in the vessel, usually downstream of the obstruction to be treated. Introduction through the guiding catheter facilitates accurate passage of the filter 4 and sheath 1 by preventing buckling and permitting easier positioning, as well as reducing the risk of dislodging clot particles from the obstruction, which is typically plaque. Then, the operator holds wire 2 stationary and retracts sheath 1, which is long enough to be accessible to the operator outside the body, until sheath 1 moves clear of filter 4, which can then expand to take on the configuration shown at 4'. Sheath 1 can then be fully withdrawn from the vessel. Whenever required, the proximal end of sheath 1 can be clamped shut, usually during withdrawal.

Figure 2:
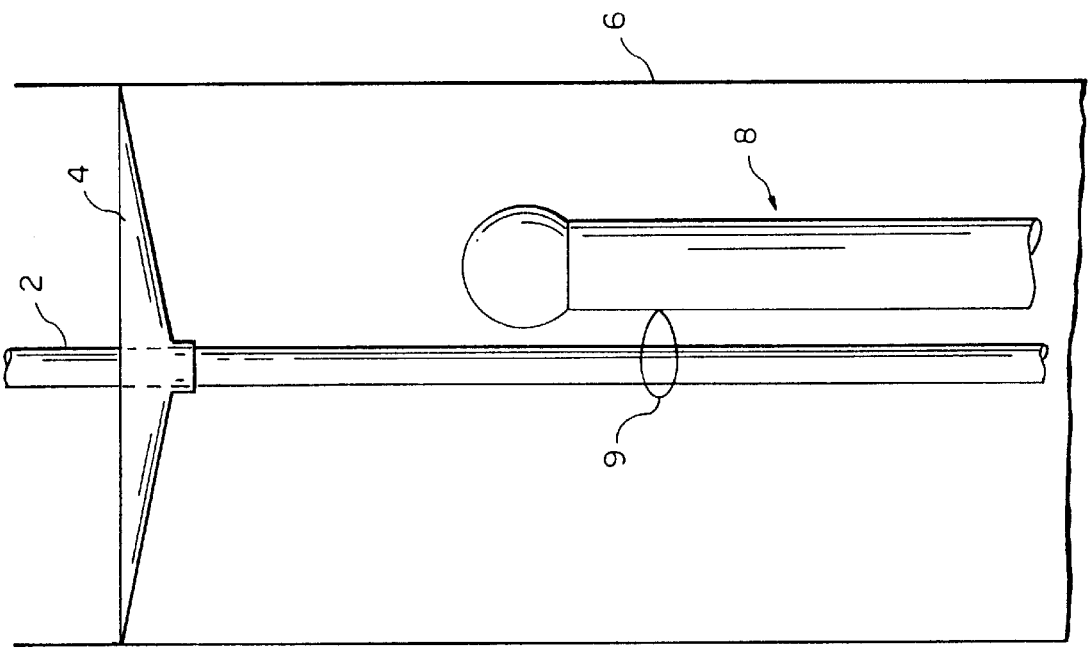
FIG. 2 is a simplified pictorial view showing the component for FIG. 1 in an expanded state, associated with a treatment device.

A second step of a method according to the invention involves performance of the desired medical treatment in the region upstream of filter 4, which region, as shown in FIG. 2, is below filter 4. Such a treatment can be for the purpose of removing an obstruction in a blood vessel 6, and this can involve any known angioplasty procedure or any known obstruction disintegration or observation (viewing) procedure employing ultrasound, laser radiation, stent placement, etc., or any mechanical cutting procedure, etc. The device for performing this function can be guided to the site by being advanced along guide wire 2.

For example, this device can be an ultrasonic device as disclosed in U.S. Pat. No. 4,870,953. This device has an output end 8 provided with a bulbous tip that applies ultrasonic vibrations to obstruction material, such as plaque or clot. Output end 8 may be guided to the site of the obstruction in any conventional manner over wire 2, however this can be assisted by providing output end 8 with a ring, or loop, 9 that is fitted around guide wire 2 before output end 8 is introduced into blood vessel 6.

After the device has been brought to the treatment site, it is operated to perform the desired treatment, in this case disintegration of plaque or clot, commonly predilation, stenting and stent dilatation. After the treatment has been performed, the treatment device is withdrawn from the blood vessel.

A third step of a method according to the invention includes positioning a second particle filter in the blood vessel upstream of first filter 4 and preferably upstream of the treatment site. This is accomplished by sliding guide wire 2 through an orifice in a second filter 14, to be described below, adjacent to a guide wire 12 that carries the second filter FIG. 3 is cross-sectional elevational view of a second unit of the protective system according to the invention for carrying out the third step.

This second unit is composed of a second tube, or sheath, 10, a second guide wire 12 and a proximal particle filter 14. Sheath 10 may have a diameter of the order of 3 mm. At the time this unit is inserted into the blood vessel, filter 4 remains in place in the blood vessel, in the expanded state as shown at 4' in FIG. 1, as does hollow guide wire 2.

Proximal filter 14 has an apex provided with a ring 16 through which guide wire 2 is inserted when the second unit is still located outside of the patient's body, in order to guide the second unit into the blood vessel up to the treatment site. Second guide wire 12 is secured to ring 16.

Prior to introduction into the patient's body, filter 14 is installed in sheath 10 in the manner illustrated in FIG. 3. The second unit is then placed over guide wire 2 and advanced into the blood vessel to the desired location.

After the second unit has been brought to the desired location, proximal filter 14 is held stationary by holding stationary the end of guide wire 12 that is outside of the patient's body, while retracting sheath 10. When filter 14 is clear of the distal end of sheath 10, filter 14 expands radially into the configuration shown at 14' to engage filter 4. This step is completed when filter 14 is fully radially expanded.

Because of the porous nature of filters 4 and 14, a reasonable volume of blood flow can be maintained in the blood vessel when the filters are deployed.

Prior to introduction of filter 14, any debris produced by the treatment performed in the second step will be conveyed by blood flowing to and through radially expanded filter 4, where the debris will tend to remain. During and after introduction of filter 14 and expansion of filter 14 into the configuration shown at 14', suction may be applied to the region between the filters through sheath 10. This will help to assure that the debris remains trapped between the two filters.

Then, in a fourth step, debris is removed from blood vessel 6 by pulling wire 2 to move filter 4 toward, and into contact with, filter 14, then retracting both filters into sheath 10 by pulling the guide wires 2 and 12, thus withdrawing the assembly of filters 4 and 14 into sheath 10. Sheath 10 with enclosed filters is then withdrawn through the guiding catheter (not shown), which is subsequently removed from the blood vessel using standard procedures. These operations are performed by pulling on guide wire 2 at its proximal end, located outside of the patient's body, while initially holding guide wire 12 stationary until filter 4, comes to nest within filter 14. Then both guide wires 2 and 12 are pulled in order to retract the filters into sheath 10. Finally, both of the guide wires and sheath 10 are pulled as a unit out of the blood vessel. During any portion, or the entirety, of this step, suction may continue to be applied to filters 4 and 14 through sheath 10.

FIGS. 4A and 4B are simplified pictorial views showing two possible arrangements for a set of filters 4 and 14. The arrangement shown in FIG. 4A corresponds to that shown in FIGS. 1, 2 and 3. The arrangement shown in FIG. 4B differs in that filter 4 is inverted relative to the orientation shown in FIGS. 1, 2, 3 and 4A. The arrangement of filters shown in FIG. 4A is applicable to short, non tortuous segments of arteries. FIG. 4B shows an optional filter arrangement for longer segments of arteries especially if they are tortuous.

When the arrangement shown in FIG. 4B is employed, filters 4 and 14 are positioned in the blood vessel by the first and third steps as described above. In order to withdraw the filters, guide wire 2 is pulled to bring filter 4 into a position in which its large diameter end has been introduced into the large diameter end of filter 14. Then, as both filters are pulled into sheath 10, filter 14 is collapsed by its contact with sheath 10 and filter 4 is collapsed by its contact with the interior of filter 14. In this form of construction, filter 14 has an expanded diameter at least slightly greater than filter 4.

The arrangement illustrated in FIG. 4B offers the advantages that in the first step filter 4 can be extracted from sheath 1 somewhat more easily and, after filter 4 has been expanded, any debris produced by the operation performed in the second step will tend to collect near the apex of filter 4, away from its line of contact with the blood vessel wall.

One exemplary embodiment of filter 4 is shown in greater detail in FIG. 5. This embodiment consist of a frame, or armature, composed of a small diameter ring 22 at the apex of filter 4, a large diameter ring 24 at the large diameter end of filter 4 and a plurality of struts 26 extending between rings 22 and 24. The frame is preferably made in one piece of a relatively thin memory metal, which is well known in the art. One example of such a metal is nitinol. The frame is constructed to normally assume a radially expanded state, such as shown at 4' in FIG. 1, but to be easily deformed so as to be retracted, or radially compressed, into sheath 1.

The frame is covered on its outer surface with a thin sheet, or membrane, 28 of suitable filter material having pores that are sized according to principles known in the art to protect organs downstream of the treatment site. The pore dimensions are selected to allow reasonable flow of blood to organs downstream of the treatment site when the filters are in place while trapping debris particles of a size capable of causing injury to such organs. The desired filtering action will be achieved with pore sized in the range of 50 $\mu$m to 300 $\mu$m. This allows different millipore sizes to be used to optimize either blood flow or embolism protection. The larger pore dimensions will be used in situations where a higher blood flow rate must be maintained and the escape of small debris particles is medically acceptable.

FIG. 6 is a view similar to that of FIG. 5 showing one suitable embodiment of filter 14, which is here shown essentially in its expanded state. Like filter 4, filter 14 includes a frame, or armature, having a small diameter ring 32 at its apex, a large diameter ring 34 at its large diameter end and a plurality of struts extending between rings 32 and 34. Filter 14 is completed by a filter sheet, or membrane, 38 secured to the outer surfaces of struts 36. Ring 32 provides a passage for guide wire 2, the passage being dimensioned to allow filter 14 to move freely along guide wire 2. Guide wire 12 is fixed to the outer surface of ring 32.

Figure 7A:
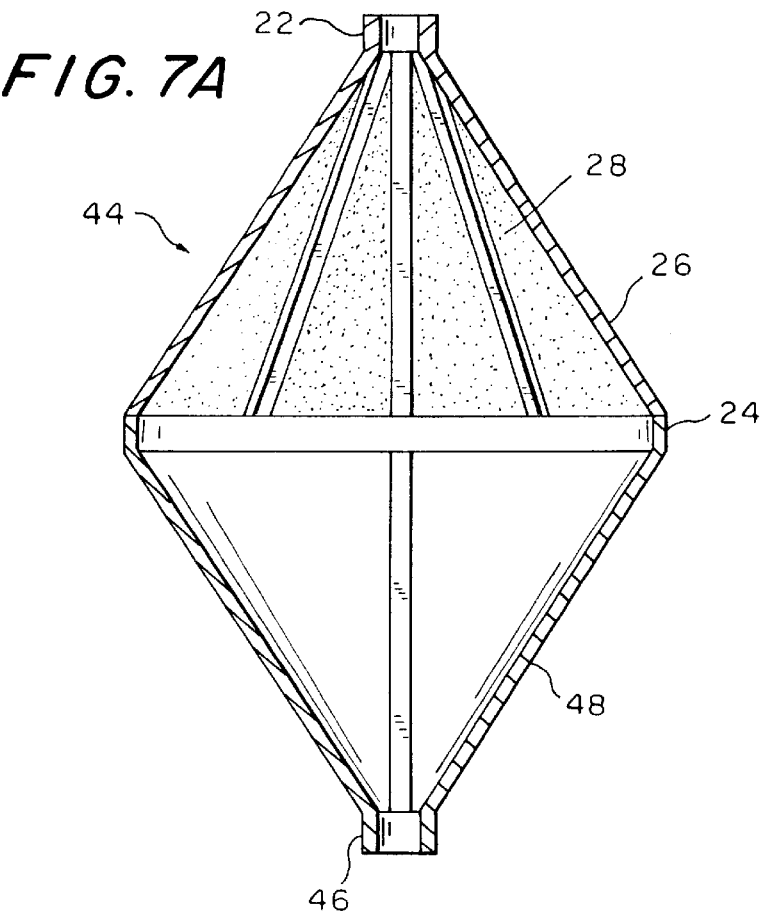
Figure 7B:
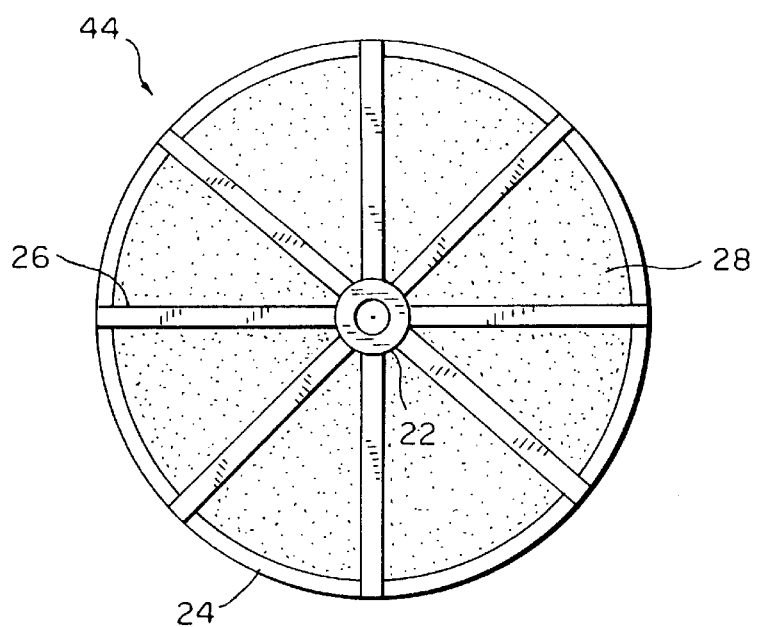
FIG. 7B is plan view of the embodiment shown in FIG. 7A.

FIGS. 7A and 7B are, respectively, an elevational cross-sectional view and a plan view of another embodiment of a distal filter 44 that can be employed in place of filter 4. This embodiment includes, like filter 4, a small diameter ring 22, a large diameter ring 24 and a plurality of struts 26, with a filter sheet 28 secured to the outer surfaces of struts 26. Here again, ring 22 has an opening for receiving guide wire 2, which will be fixed to ring 22.

Filter 44 is further provided with a second, small diameter, ring 46 and a second series of struts 48 extending between rings 24 and 46. Ring 46 has an opening with a diameter larger then that of guide wire 2, so that ring 46 is moveable relative to guide wire 2.

All the parts of filter 44, except for membrane 28, like the corresponding parts of filter 4 and 14, may be made in one piece of a memory metal that has been processed to bias the filter toward its radially expanded configuration. All of these components are sufficiently thin to allow the filter to be easily collapsed radially within its respective sheath 1 or 10. Filter 44 will be mounted so that its apex faces in the distal direction, i.e. the cone formed by the struts 26 and filter sheet 28 have an orientation which is opposite to that of filter 4.

Filter 44 is brought to its radially expanded state in essentially the same manner as filter 4. When the filter portion is at the desired location in the blood vessel, sheath 1 will be retracted in order to allow filter 44 to expand radially. When the filters are to be withdrawn, guide wire 2 is pulled in the proximal direction until the lower part of filter 44, composed of ring 46 and strut 48, comes to nest either partially or fully in filter 14. Then, both guide wires 2 and 12 can be pulled in the proximal direction in order to retract the filters into sheath 10. During this operation, ring 46 has a certain freedom of movement relative to guide wire 2, which will help to facilitate the radial contraction of filter 44. Alternatively, or in addition, sheath 10 can be advanced in the distal direction to assist the retraction operation.

According to further alternatives, rings 22 and 46 can be dimensioned so that either guide wire 2 is fastened to ring 46 and movable longitudinally relative to ring 22, or guide wire 2 is fixed to both rings 22 and 46. In the latter case, radial contraction and expansion of filter 44 will still be possible in view of the flexibility and deformability of its components.

Figure 8:
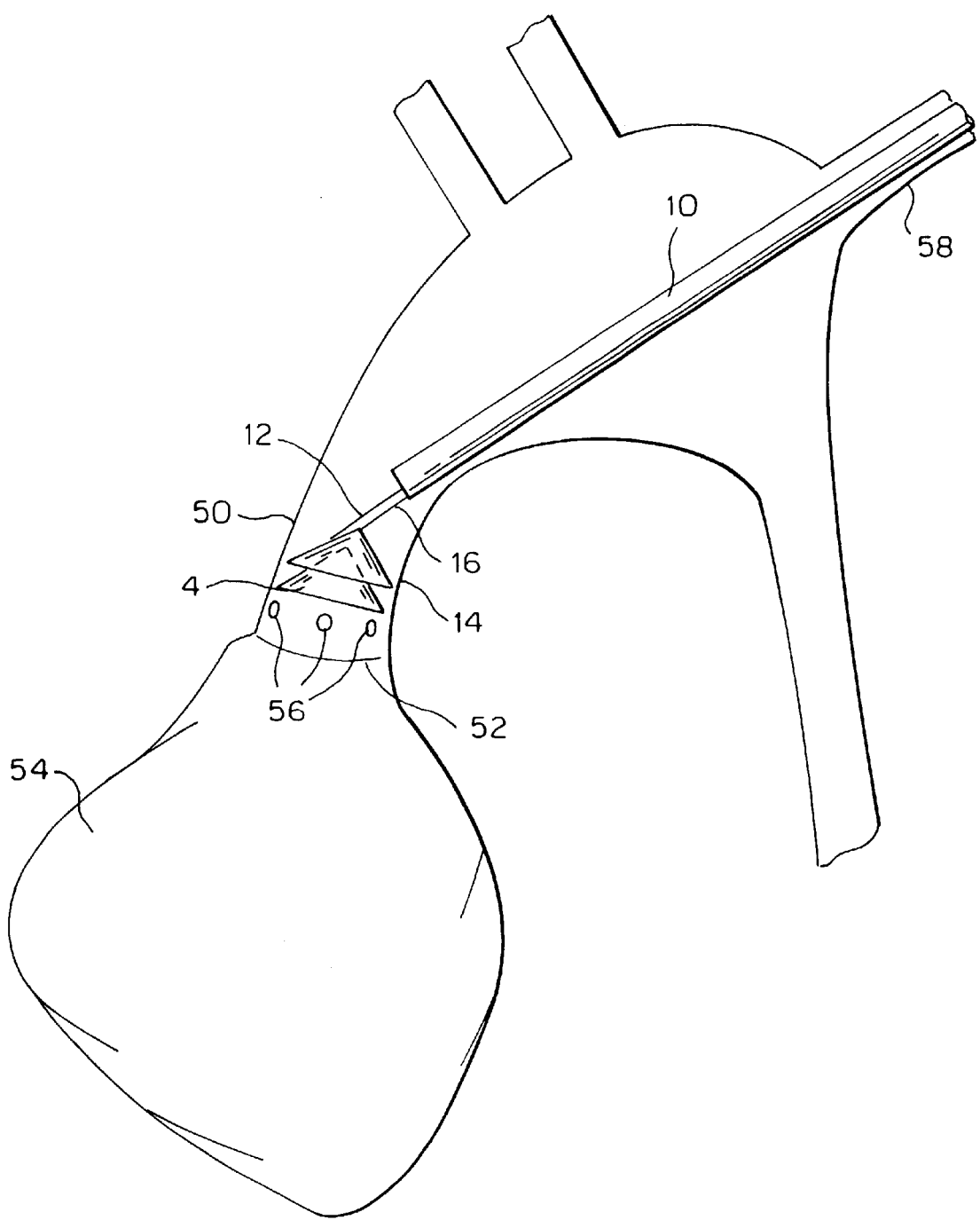
FIGS. 8, 9 and 10 are simplified pictorial views illustrating specific procedures that may be carried out with a system according to the invention.

A system according to the invention can be used, for example, to improve the safety of bypass surgery. Referring to FIG. 8, an example of that surgery involves attaching vein bypass grafts to the aorta 50 starting from a point just downstream of the aortic valve 52 located between the left ventricle and aorta of the heart 54. In such a procedure, holes 56 are cut in aorta 50 for insertion of the upstream ends of the grafts. The operation of cutting into the wall of the aorta to sew on grafts can produce debris that will be carried along with blood flowing through the aorta to locations in the circulatory system where it can create an embolism in various organs, including the brain.

Referring to FIG. 8, the risk of such an occurrence can be reduced by introducing a system according to the embodiment of FIGS. 1–3, before holes 56 are cut, through a subclavian artery 58, which can be accessed via the patient's arm, and the brachial artery, to bring filters 4 and 14 to a location downstream of the location where holes 56 will be cut and to expand those filters so that they extend across the blood flow path through the aorta. Then, when holes 56 are cut, any debris produced by the cutting operation will be trapped, at least initially, within filter 4. However, while both filters are being withdrawn into tube 10, after holes 56 have been cut and possibly after vein grafts have been sutured to the holes, some debris may be squeezed out of filter 4, even as suction is being applied through tube 10. If this should occur, the debris can be drawn into filter 14 so as to be safely removed from the circulatory system.

Figure 9:
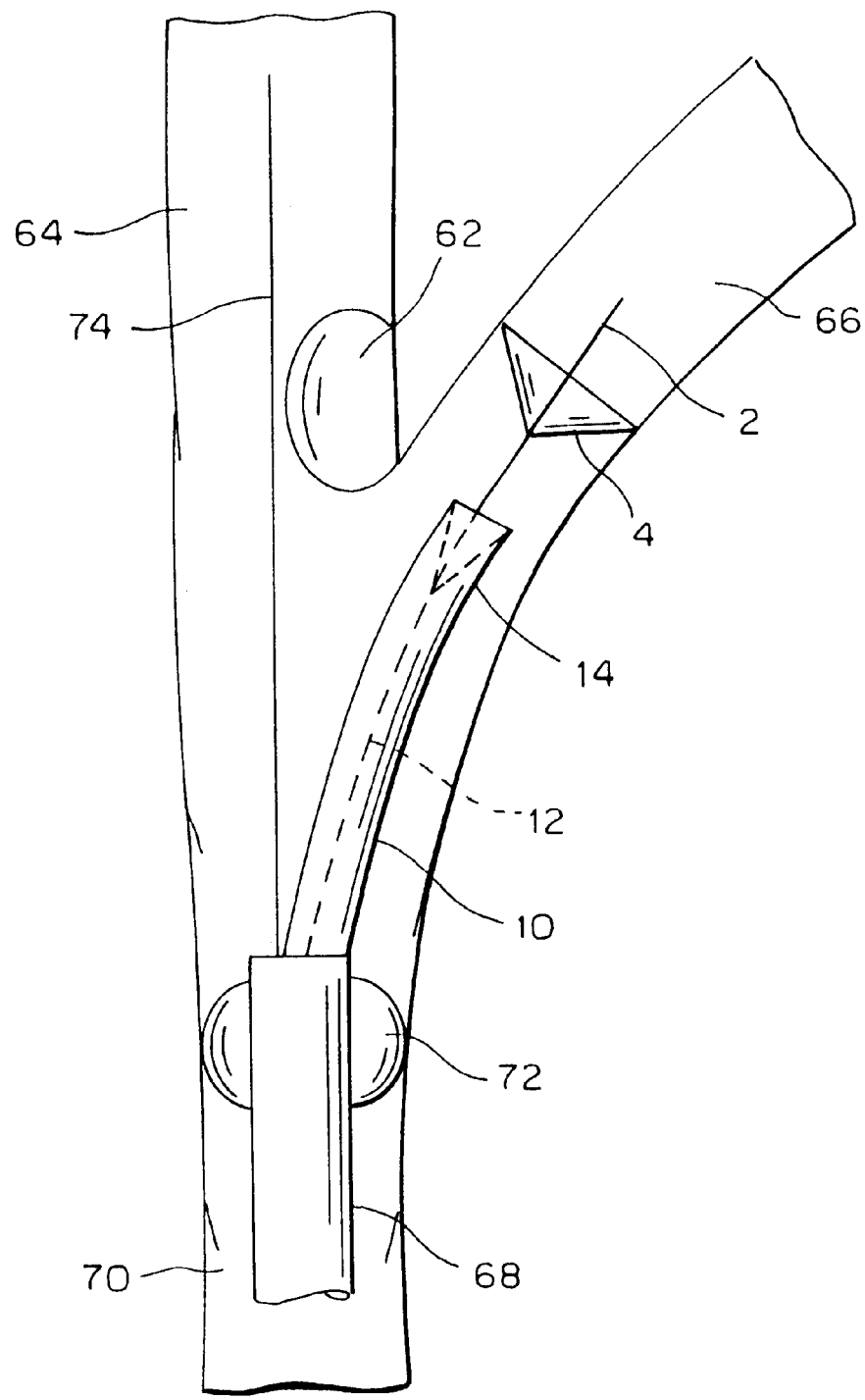

Another example of the use of a system according to the invention to capture debris incident to a medical procedure is illustrated in FIG. 9. A plaque deposit 62 is present on the wall of an internal carotid artery 64 just downstream of the junction with an associated external carotid artery 66. A guiding catheter 68 is introduced into common carotid artery 70 and is used as a conduit for introducing all other devices required to removes plaque 62 and collect the resulting debris. Catheter 68 carries an annular blocking balloon 72 on its outer surface and is provided with a conduit (not shown) for supplying inflation fluid to balloon 72.

A wire 74 carrying a Doppler flow sensor is introduced into internal artery 64 to position the flow sensor downstream of plaque 62. Then, sheath 1 (not shown) is introduced to deploy filter 4 in external artery 66, as described earlier herein and balloon 72 is inflated to block blood flow around catheter 68. After filter 4 is deployed and balloon 72 is inflated, any conventional procedure, such as described above with reference to FIG. 2, can be carried out to disintegrate plaque 62.

Then, as described with reference to FIG. 3, sheath 12 is advanced through catheter 68 to the location shown in FIG. 9, filter 14 is deployed and expanded into internal artery 66, and suction is applied as filters 4 and 14 are retracted into sheath 10.

In this procedure, starting from a time before disintegration of plaque 62, blood flow through common carotid artery 70 is blocked by inflated balloon 72. This results in a retrograde flow in internal artery 64 back toward common artery 70 and then antigrade flow into external artery 66, where debris being carried by the blood flow will be trapped on filter 4. The pressure sensing wire 74 is used to ascertain the collateral pressure, which must always exceed 40 mm Hg in the carotid. After a sufficient period of time has elapsed, filter 14 will be deployed to nest against filter 4 and both filters will be retracted into sheath 10 while suction is applied, possibly through sheath 10. Then, balloon 72 will be deflated, sheath 10 will be withdrawn through guide catheter 68 and catheter 68 will be withdrawn.

In another application of the invention, the filters can be passed through a small peripheral artery into the aortic root to entrap debris generated during cardiac surgery. Such a device can be used during surgery or can be implanted for long-term use to prevent migration of blood clots to the brain under certain circumstances, such as during atrial fibrillation.

Figure 10:
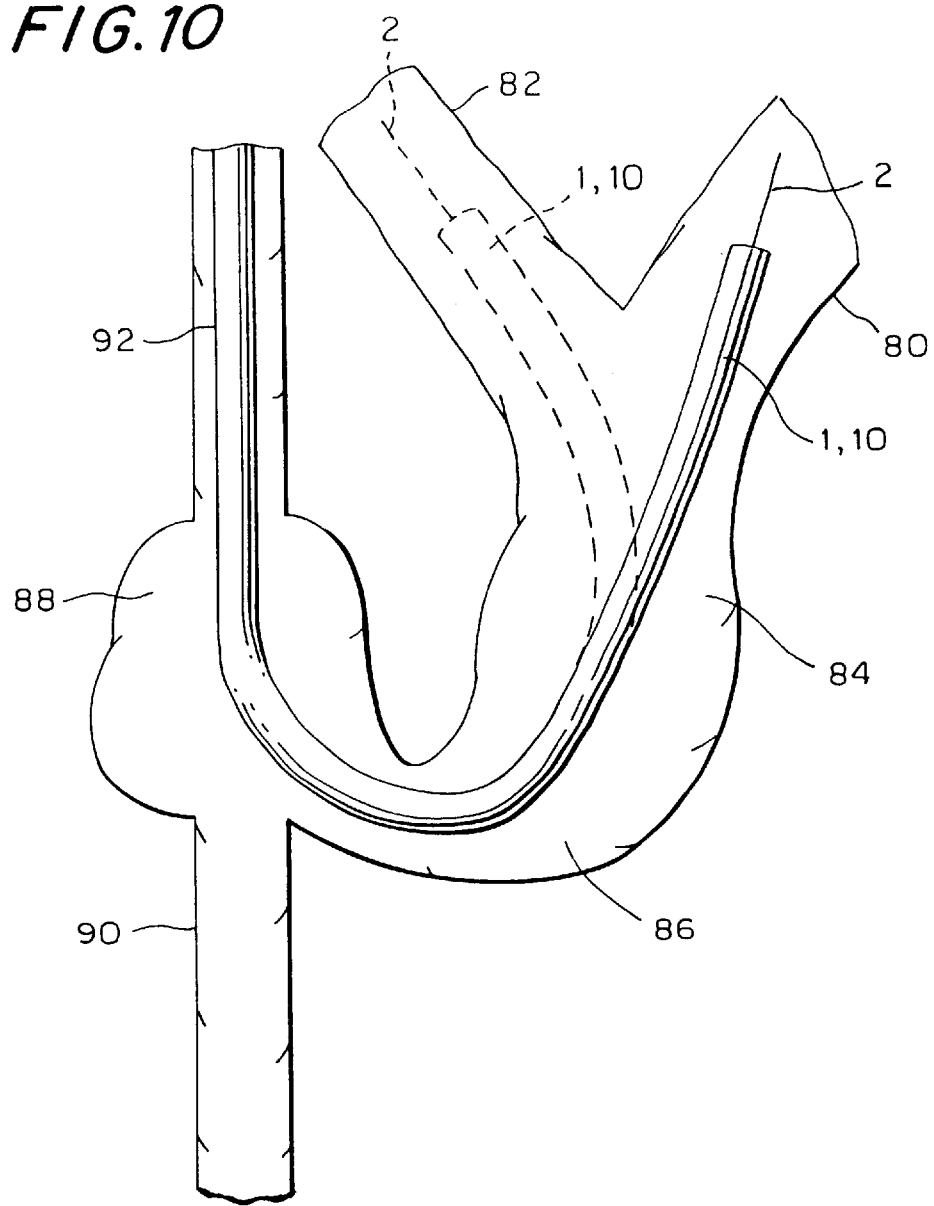

A further example of procedures that may be carried out with a device according to the invention is illustrated in FIG. 10, which shows the positioning of a device according the invention for treating an obstruction in an artery 80 or 82 emerging from the pulmonary artery 84 connected to the right ventricle 86 of a patient's heart. The right ventricle communicates with the right auricle 88 of the heart, which is supplied with blood from veins 90 and 92. In such a procedure, sheaths 1 and 10 may be introduced through either vein 90 or 92 and then through auricle 88, ventricle 86 and pulmonary artery 84 into either one of arteries 80 and 82 to be treated. Techniques for guiding the sheaths along the path illustrated are already well known in the art. Once positioned in the appropriate artery 80 or 82, an obstruction removal procedure will be performed in the manner described above.

Figure 11:
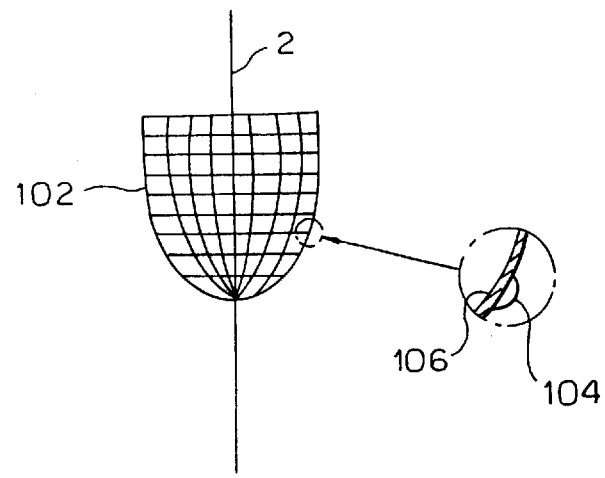
FIG. 11 is an elevational view of another embodiment of a filter component of a system according to the invention.

FIG. 11 shows another embodiment of a filter component according to the invention in the general form of a basket, or cup, 102 made of a layer 104 of a radially compressible, autonomously expandable, material, such as a memory metal, and a filter sheet 106. Layer 104 may be fabricated by weaving memory metal wire into a mesh, or screen. Filter sheet 106 is made of a suitable plastic material, such as polyester, perforated to provide the desired filter pores, having dimensions described above. The bottom of basket 102 may be fixed to guide wire 2, in the manner of filter 4, described above, or may have a circular opening that is slidable along wire 2, with a second guide wire attached to the edge of the opening, in the manner of filter 14, as described above. Each such basket 102 will be used in the same manner as a respective one of filters 4 and 14 and will be dimensioned to extend across the blood vessel at the location where the system is to be employed.

The procedures described above are merely exemplary of many procedures that can be aided by utilization of the system according to the present invention and other uses will be readily apparent to medical professionals. It should further be clear that the examples shown in the drawings are illustrated in a schematic form. For example the shape of the ring 24 in FIGS. 5, 7A and 7B is shown as a circle. However, for a ring that has to be collapsed to allow the filter to be pulled it into the sheath, it would be more logical to give it a slightly wavy or corrugated shape. This would make it more flexible and capable of smooth radial contraction and expansion. Another embodiment of a system having a distal protection system with a double filter according to the invention is shown in FIGS. 12–16.

In FIGS. 12–14, a circularly cylindrical tube 150 is formed to have, at one end, which is here its distal end, a monolithic, or one-piece, distal filter that has a tubular conical shape with a pattern of slots that have been made in the surface of tube 150 by cutting, grinding, etching or any other technique. Tube 150 can be made of any material, like metal or polymer, and especially of nitinol with superelastic properties. Tube 150 may be long enough to be used as a guiding rail for catheters that are used for the angioplasty/stenting procedure.

At the distal end of tube 150, the slots are cut in such a way as to form a filter that has an expansion capability of at least, for example, a factor of 4. If tube 150 is made of nitinol, the expanded shape can be programmed into the memory by a heat treatment, while the material is kept in the desired expanded shape, shown in FIGS. 13 and 14, by some restraining tool. This is a known technique called shape setting.

The slots cut at the distal end of tube 150 leave thin, circularly curved, circumferential groups of distal strips 110 and groups of intermediate strips 130, 131 and 132. These strips are connected to, and interconnected by, thicker longitudinally and radially extending groups of struts 120, 140, 141 and 142 that end at the continuous, i.e., imperforate, surface of tube 150. Upon expansion for shape setting, struts 120, 140, 141 and 142 will bend out and give the distal section of tube 150 a conical shape. The thinner strips 110, 130, 131 and 132 will deform to follow circular arcuate paths during shape setting.

Tube 150 may have a length sufficient to have its proximal end (not shown) extend out of the patient's body where the surgeon can manipulate it. Tube 150 can also be shorter and attached to a separate guide wire to save costs or to reduce the diameter over the majority of the length.

The geometry of the strips and struts is chosen so that deformation upon shape setting and during expansion/contraction stays below acceptable limits. If necessary the cutting pattern of the strips can include some solid hinges. These are preferential bending spots, created by locally reduced thickness of the material. In this way it is also possible to cause a proper folding up of the strips while the filter is forced back into the cylindrical shape after conical shape setting.

In FIG. 12 the filter at the distal end of tube 150 is shown in its folded, or radially compressed, state, as it would appear when installed in sheath 1 of FIG. 1. FIGS. 13 and 14 show the final shape of the filter after shape setting and then after deployment from sheath 1. Distal strips 110 create a non-traumatic rim with a smooth series of tangential connections between the struts 120. The series of strips 130, 131 and 132 connect the long struts 120, 140, 141, and 142 together at different intermediate positions, but in principle intermediate strips 130, 131 and 132 could be omitted, at least if there are a sufficient number of longitudinal struts 120, 140–142 to create the desired fine mesh. However, the feasible number of struts is limited by the following parameters:

The initial tube diameter;

The minimum width of each slot, determined by the tooling;

The minimum required width for a stable strut; and

The desired expansion ratio determined by the acceptable length of each strut.

If the filter pores, constituted by the slots, are not fine enough, because the open area between the struts of an expanded filter becomes too large, additional circumferential groups of strips can be provided to make the mesh finer. The number of strips can be chosen freely, because they do not have an influence on the expansion ratio. For clarity only four rows of strips are shown in FIGS. 12–14. As can be seen, the length of the strips changes from proximal to distal. For example, strips 130 are longer than strips 131 and 132.

FIG. 14 shows a top view of the expanded filter where the strips 110 have been shape set to create a smooth rim that can perfectly cover the whole cross section of an artery with a good fit.

The conical filter shown in FIGS. 12–14 is meant to be used in combination with a delivery sheath, as described herein with reference to FIG. 1. Such a sheath can run over the surface of tube 150 and if the sheath is retracted, the filter will assume the conical shape shown in FIGS. 13 and 14, which is substantially the same as the shaping pattern of FIG. 1. When such a delivery sheath, surrounding a collapsed filter, is brought into an artery and then gently withdrawn, the filter will open up, flare out and completely obstruct the cross section of the artery. Nitinol is an excellent material for such a filter, because it can withstand high elastic strains. A nitinol filter according to this design can be deployed and collapsed elastically several times without any plastic deformation, whereas known filter materials would fail.

Figure 15:
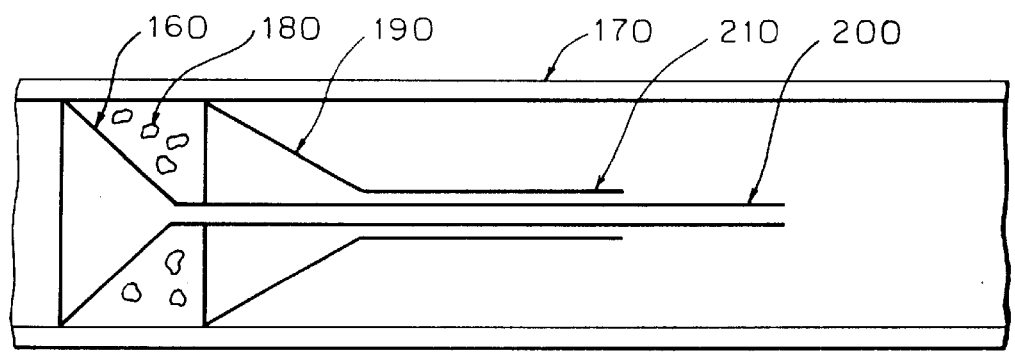
FIG. 15 is a simplified side cross-sectional view showing the other embodiment of a system in a blood vessel with two filters of the type shown in FIGS. 12–14.

In FIG. 15 a pair of filters 160 and 190 each having the form shown in FIGS. 12–14 according to the invention are used in combination in order to entrap emboli particles between them for removal from the artery.

During the major part of an angioplasty/stenting procedure, only the most distal filter 160 is in place. During angioplasty/stenting of the artery 170, emboli particles 180 may be released from the lesion site and move with the blood stream until they are stopped by filter 160. At the end of the procedure, a second filter 190 is advanced over the wire or tube 200 that is connected to filter 160. The diameters of the distal ends of filters 160 and 190 are about the same, and filter 190 can completely be advanced over filter 160, when it is delivered from its own delivery sheath (not shown). Filter 190 has its own tube 210, which has a much larger inner diameter than the outer diameter of wire or tube 200 of the first filter 160. The lumen between both tubes 200 and 210 can be used for flushing/suction. Of course this can also be performed through tube 200 as well.

Figure 16:
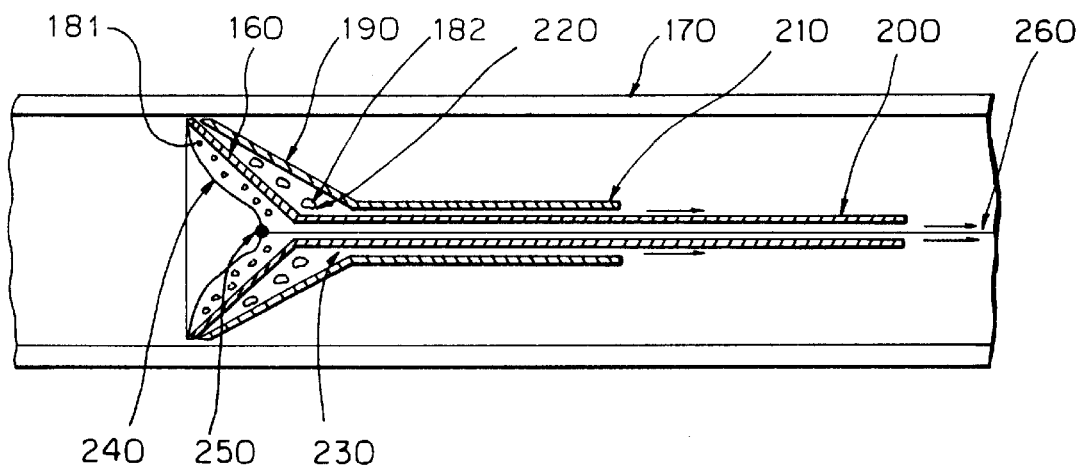
FIG. 16 is a view similar to that of FIG. 15 showing a modified form of construction of the system shown in FIG. 15.

FIG. 16 shows the system of FIG. 15, with the thickness dimensions of the various components illustrated more clearly, at a point in a procedure just after the second filter 190 has been brought into a position to enclose the first filter 160, with the distal ends of both filters in contact with one another. The opening angles of both filters may be identical or, as shown, different. In case they are identical, the surfaces of both filters will mate perfectly and all debris will be trapped, like in a sandwich, between the two conical surfaces.

However, if the cone of the second filter 190 has a smaller opening angle than filter 160, as shown, the situation shown in FIG. 16 will result. The distal edges of both filters fit well together, but for the rest there is a gap between the surfaces of the two filters. This gap creates a chamber 220, in which small particles can freely move. The advantage of this arrangement is that the particles can be removed from chamber 220 by suction through the lumen 230 between tubes 200 and 210.

FIG. 16 further shows an additional filter sheet 240 that is used to capture fine particles that go through the holes in filter 160. The holes in the filter 160 can for example have a maximum size of 250 μm, while filter sheet 240 can be provided with holes, or pores, having a size of the order of only 150 μm or less, dependent on the application.

Filter sheet 240 may be made of a fine metal sheet, a polymer, or any other flexible tissue and it can be attached to the distal strips 110 of filter 160 by means of glue, stitching or any other means. At its proximal extremity, corresponding to its center, sheet 240 may a central connection point 250 that is connected to a long wire 260 that runs completely through tube 200 to a location outside of the patient's body. With this wire 260, filter sheet 240 can be pulled into a conical configuration before filter 160 is pulled into its delivery sheath (not shown). This makes it easier to bring filter 160 and filter 240 into a smooth collapsed state. Once filter 160 is deployed, or expanded, wire 260 may be released a little bit to enable filter sheet 240 to move away from filter 160, thus creating additional space for entrapment of the small particles 181 that fit through the holes in filter 160. The larger particles 182 will not go through filter 160 and will stay at the proximal side of this filter. If chamber 220 between the conical surfaces of filters 160 and 190 is large enough, and if wire 260 of filter sheet 240 is not pulled too tight, most particles can easily be suctioned out through lumen 230. By pulling wire 260, the particles 181 will be forced to move in the direction of the suction opening. This is another advantage of the use of a movable filter sheet 240.

Finally only some very large particles will remain in chamber 220, and they can be removed by holding them entrapped between the surfaces of the filters, while both filters are pulled back into the delivery sheath and the filters are compressed, or collapsed to their cylindrical configurations. This is done while continuous suction is applied.

In case the large particles are squeezed, break up and slide through the holes in filter 160, they will again be gathered in filter sheet 240. Eventually wire 260 can be released even more if there is a lot of material between filter 160 and filter sheet 240. In that case, filter sheet 240 may look like a bag, filled with material, that hangs on the distal side of the completely collapsed filter 160. This bag may not be pulled back into the delivery sheath, but will just be pulled out of the artery while it hangs at the distal tip of the sheath.

A major advantage of this double filter design is that upon compression of the filter cones, the emboli particles can only leave the chamber 220 through the suction lumen 230, or they stay there to be finally entrapped mechanically between the cone surfaces or to remain in the bag.

The distal filter will be in place during the whole procedure of angioplasty/stenting and therefore the mesh size is very important. An additional pressure-measuring tip, distally in the blood stream may monitor perfusion. The wire that holds this tip may be integrated with wire 260 that is controlling the filter sheet 240. Alternatively, wire 260 can have the form of guide wire 2 shown in FIG. 1, with a lumen connected to a pressure detector.

On the other hand, filter 190 is only used a very short time and therefore its mesh size may even be finer than that of filter 160.

In general, filter systems according to the invention can have many embodiments, including systems containing a distal filter with or without an additional filter mesh with a proximal filter, also with or without an additional filter sheet. Also the relative position of filter and filter sheet can be varied. The sheet can be outside of filter 160. Further embodiments can be combinations of emboli catching devices of different geometries and/or types. Filters, balloons and sponges of all kinds can be used in multiple combinations, all based upon the principle of full entrapment of particles before the protection device is collapsed upon removal from the patient's body. Combinations of an inflatable delivery sheath according to the invention with a multi-filter arrangement, as disclosed, are also meant to be an embodiment of this invention.

FIGS. 17–27 illustrate the structure and successive phases in the use of another embodiment of the invention that is suitable for performing angioplasty procedures while trapping and removing debris produced by the procedures.

Figure 17:
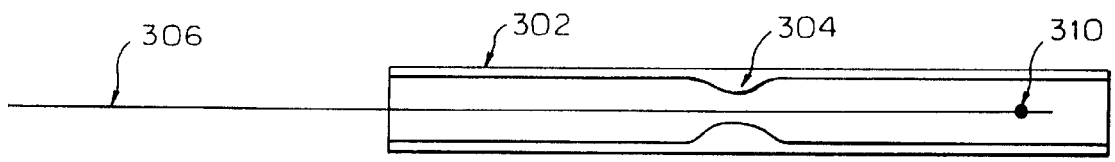
FIGS. 17–27 are simplified pictorial views showing successive stages in an angioplasty and stenting procedure using an embodiment of a system according to the invention.

FIG. 17 shows an artery 302 with an obstruction, or lesion site, 304 that reduces the effective diameter of artery 302. The invention can be used to treat virtually any artery throughout the body, such as for example the inner carotid artery where emboli are extremely dangerous because the particles can cause stroke in the brain.

A first component of this embodiment is a guide wire 306 that, in a first step of a procedure using this embodiment, is advanced through artery 302, normally in the direction of blood flow, and past lesion site 304. The blood pressure in artery 302 adjacent the distal end of guide wire 306 can be monitored by a pressure monitoring device that includes a miniature pressure sensor, or transducer, 310 at the distal end of guide wire 306 and a signal measuring unit at the proximal end, as represented by element 5 in FIG. 1. Guide wire 306 can be provided with a longitudinal lumen that can contain wires or an optical fiber to transmit electrical or optical signals from sensor 310 to the signal measuring unit and the signal measuring unit can be connected to a conventional indicator, display and/or warning device. Sensor 310 may be, for example, a distal miniature load cell, possibly of the type having a load-dependent electrical resistance. The pressure monitoring device can continuously monitor the blood pressure in artery 302 during an entire procedure.

Figure 18:
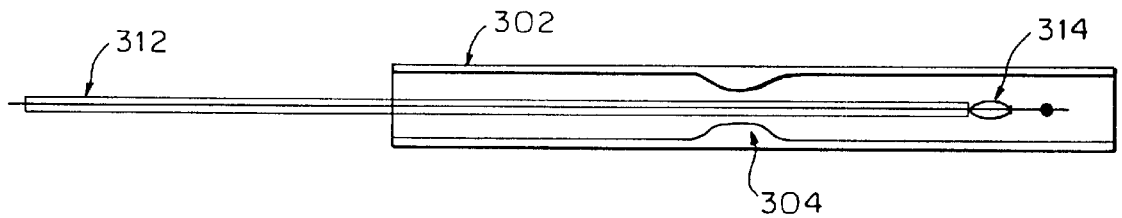

FIG. 18 shows the second step in which a guiding catheter, or sheath, 312 having a longitudinal lumen carrying a distal protection means 314 is advanced over guide wire 306 until means 314 reaches a location that is distally, or downstream, of lesion site 304. If distal protection means 314 is a filter made from a small slotted nitinol tube, it can be advanced over guide wire 306 while retained in the lumen that extends through catheter 312.

Distal protection means 314 may be a filter, as described earlier herein, or a blocking balloon, or possibly a compressible sponge element. For example, means 314 may be an expandable filter cone, or umbrella, having the form disclosed, and deployed and retracted in the manner disclosed, earlier herein with reference to FIGS. 1–14, and particularly FIGS. 12–14, held in its collapsed state within catheter 312. If distal protection means is a balloon, it will be connected to an inflation lumen formed in or carried by catheter 312.

Figure 19:
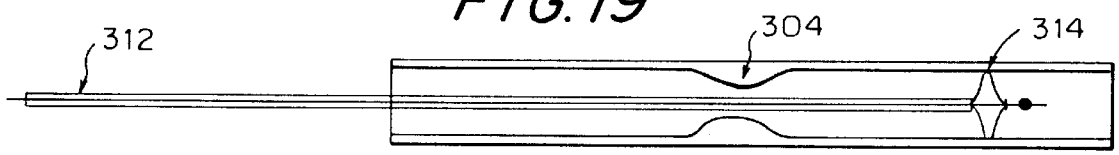

In the next step, depicted in FIG. 19, the distal protection means 314 is deployed until it extends completely across the blood flow path defined by artery 302 in order to catch all emboli particles that may be released from the lesion site upon the following steps of the procedure. Protection means 314 will stay in place until the end of the procedure.

Figure 20:
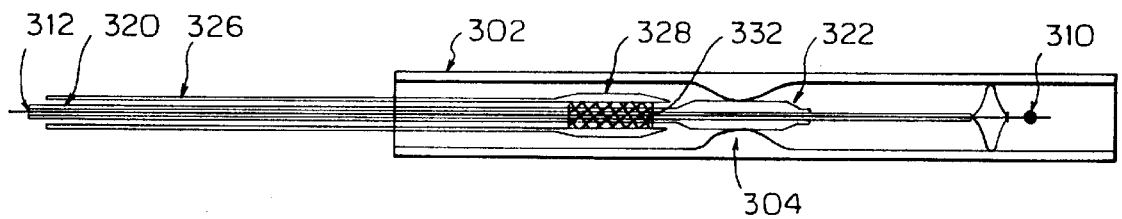

FIG. 20 shows the following step in which a predilatation catheter 320 is introduced over guiding catheter 312. Predilatation catheter 320 carries, at its distal end, a predilatation balloon 322. Predilatation catheter 320 can be advanced over guiding catheter 312 and has several purposes. First, its predilatation balloon 322 can be used to enlarge the inner diameter of lesion 304 in order to create sufficient space for positioning a postdilatation device 326 in the form of a sheath carrying an inflatable balloon section 328. Section 328 may, if desired, carry a stent 332 that is initially in a radially contracted, or collapsed, state. Furthermore the distal tip of the catheter 320 with balloon 322 can act as an internal support for the postdilatation balloon 328. The inner wall of device 326 constitutes a delivery sheath within which self-expanding stent 332 is retained prior to deployment and out of which stent 332 can by pushed by some conventional delivery means (not shown). Such a delivery means for self-expanding stents can be of any kind, for example a pusher-wire that pushes against the proximal side of the stent to push it out of the sheath.

Figure 21:
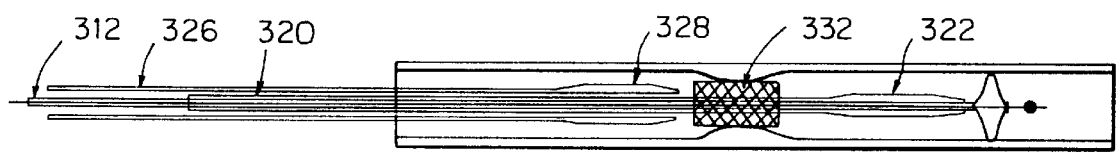

FIG. 21 shows the subsequent step in which predilatation balloon 322 has been deflated and advanced in the distal, or downstream, direction. Self-expanding stent 332 has been pushed out of delivery sheath 326. Normally, a delivery sheath only serves to bring a stent in its compressed state to the lesion site and to hold it compressed until it is to be deployed. This sheath generally has a cylindrical shape and upon delivery of the stent the sheath is pulled back, while the self-expanding stent leaves the distal tip of the delivery sheath. The sheath is then removed from the patient's body. The stent may have enough radial expansion force to fully open at the lesion site, but often this force is insufficient and the stent will stay in some intermediate semi-deployed position. A self-expanding stent can be made of several types of material, for example nitinol. Nitinol is a material with mechanical hysteresis and the force needed to collapse the stent is much higher than the radial force that the stent exerts upon deployment. This means that a nitinol self-expanding stent may be strong enough to hold an artery open, but it may need some help to reach full deployment. This help can come from postdilatation balloon 328.

Figure 22:
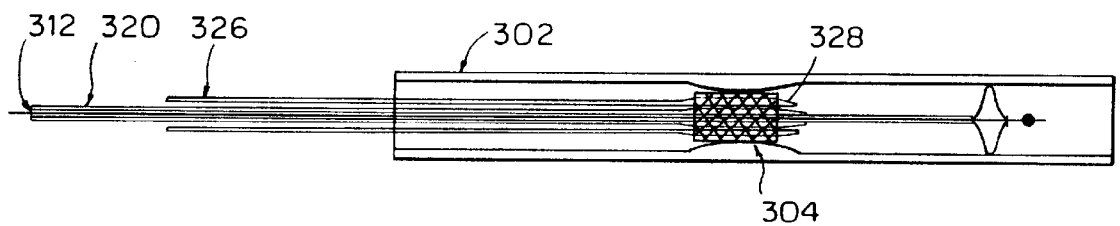
Figure 23:
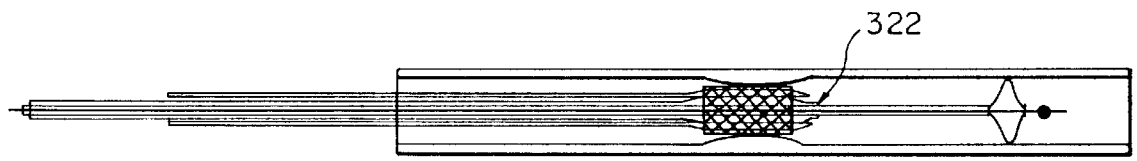

FIG. 22 shows the next step in which sheath 326 is used to help deploy stent 332. The distal end of sheath 326 with balloon section 328 can be inflated through a lumen (not shown) in the sheath wall. First the delivery sheath 326 is advanced again and the balloon area 328 is lined up with stent 332 in lesion site 304. Inflation of balloon section 328 will now cause further expansion of stent 332. However, the inner wall of sheath 326 that held stent 332 before delivery may collapse under the high pressure that may be needed to fully deploy stent 332. Therefore, predilatation balloon 322 can be inflated to be used to create a stiffer inner support for sheath 326. By lining up of both balloon sections, as shown in FIG. 23, a concentric double balloon segment is created, which is strong enough for post-dilatation.

Figure 24:
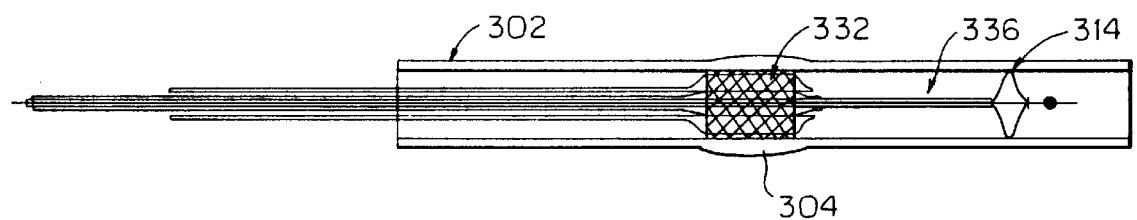

FIG. 24 show the next step in which stent 332 is fully deployed by the combined forces of balloon 322 and postdilatation balloon section 328, despite the opposing forces of the artery wall at lesion site 304 that now has become a larger opening. If distal protection means 314 is a balloon and if balloon section 328 causes full proximal occlusion, a closed chamber 336 is created in artery 302 between balloon 314 and balloon section 328.

Figure 25:
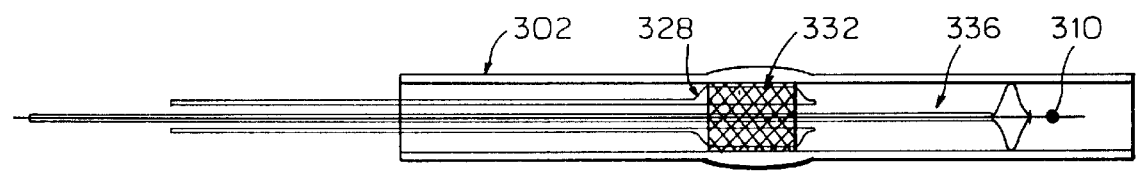
Figure 26:
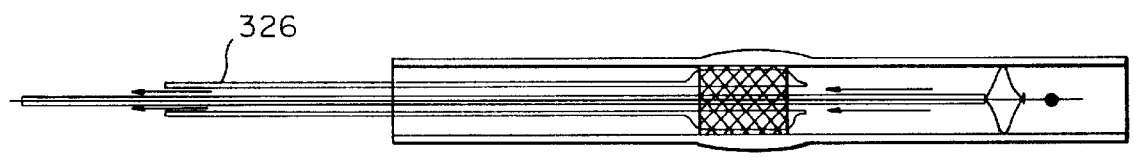

FIGS. 25 and 26 show the next step in which predilatation catheter 320 has been removed, leaving inflated balloon section 328 around delivery sheath 326 in place. Although the internal support for sheath 326 has been removed, inflated balloon section 328 can easily be used for proximal occlusion means, because the pressure may be much lower than for postdilatation of the lesion and stent deployment. Sheath 326 that held stent 332 before can now be used as a working channel, e.g. for flushing and suction. This working channel is in open connection devices outside of the patient's body and can be used for a series of procedures in the closed chamber 336 between balloon 314 and balloon section 328. One advantage of this closed chamber is that it can be flushed with a clear solution having a composition that can dissolve the plaque without danger for downstream body parts. Such compositions are known in the art. After flushing with a clear fluid the artery wall in the chamber region can be inspected with an endoscope or an optical fiber. This enables visual inspection under clear sight in a closed compartment of the artery including inspection of the stent surface. As long as the pressure behind the distal occlusion device is monitored, it is a safe way to work.

If desired, the inflatable delivery sheath/suction tube 326 can be deflated, pulled back until it is proximal of the stent section and then be re-inflated to enable additional flushing, suction and inspection, while the distal occlusion device 314 is still in place.

For supply of flushing fluid, a separate lumen can be made in the wall of delivery sheath 326, running to the distal end of this sheath (not shown). Other procedures in a temporary closed chamber of an artery include ultrasonic treatment, radiation therapy and drugs delivery, among others.

Figure 27:
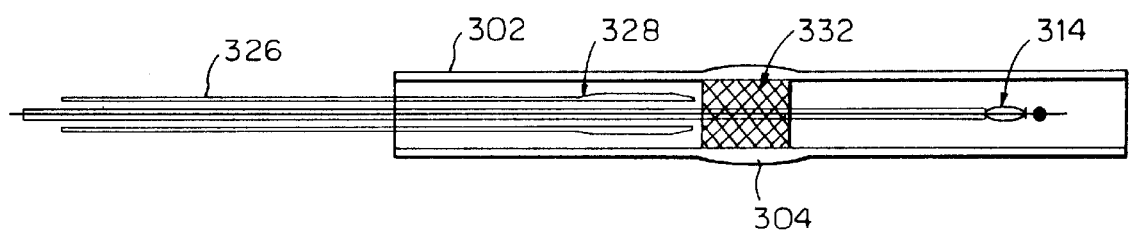

FIG. 27 shows a final step in which postdilatation balloon section 328 has been deflated and distal protection means 314 has been collapsed. The final step can be the removal of all devices from the patient's body, except, of course, stent 332, which can stay there.

As explained above, the number of longitudinal struts is limited on the basis of the desired expansion ratio. The distance between two circumferential strips can be made rather small, but they must still be able to be bent in order to get a collapsable and expandable device. Therefore a certain gap must remain between them. Normally such a gap would be larger that 50 μm, so an additional filter mesh is required in case the allowed particle size is 50 μm, such as for use as a filter in a carotid artery.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A system for preventing embolism and microembolism in a vascular system, said system comprising:
   an elongated support element;
   a first filter element with millipores carried by said support element and radially expandable from a closed condition to an open condition;
   a second filter element surrounding said support element and radially expandable from a closed condition to an open condition; and
   means coupled to at least one of said filter elements for moving said at least one said filter elements between its respective closed and open conditions independently of movements of the other one of said filter elements between its respective closed and open conditions,
   wherein each of said filter elements has a filter surface structured to prevent passage of particles and permit passage of blood.

2. The system of claim 1 wherein each of said filter elements has an outer edge concentric with said support element.

3. The system of claim 2 wherein at least one of said filter elements comprises:
   an armature of a resiliently deformable material; and
   a sheet of filter material secured to said armature and providing said filter surface.

4. The system of claim 3 wherein said at least one of said filter elements has a generally conical or trumpet shape form with a vertex, said vertex being located adjacent said support element.

5. A system for preventing embolism and microembolism in a vascular system, said system comprising:
   an elongated support element;
   a first filter element with millipores carried by said support element and radially expandable from a closed condition to an open condition; and
   a second filter element surrounding said support element and radially expandable from a closed condition to an open condition,
   wherein:
      each of said filter elements has a filter surface structured to prevent passage of particles and permit passage of blood;
      each of said filter elements has an outer edge concentric with said support element;
      at least one of said filter elements comprises:
         an armature of a resiliently deformable material; and
         a sheet of filter material secured to said armature and providing said filter surface; and
      the material of said armature is an expandable memory metal and said armature is shaped to be in an unstressed state when said one of said filter elements is in the open condition.

6. The system of claim 5 wherein said armature is formed by shape setting.

7. The system of claim 6 wherein said memory metal is nitinol.

8. The system of claim 5 wherein said support element has two opposed ends and a lumen that extends between said ends, and said system further comprises a pressure sensor in communication with the lumen at one of said ends.

9. The system of claim 1 wherein at least one of said filter elements comprises a basket of a resiliently deformable material having pores dimensioned to prevent passage of particles and permit passage of blood.

10. The system of claim 1 wherein:
    said device is adapted to be inserted into a blood vessel of a patient;
    said elongated support element has a distal end adapted to be inserted into the blood vessel and a proximal end adapted to be located outside the patient when said device is in use;
    said first filter element is located in proximity to said distal end of said elongated support element; and
    said second filter element is disposed at a location proximal to said first filter element and is movable relative to said support element.

11. The system of claim 10, further comprising a displacement member secured to said second filter element for displacing said second filter element relative to said support element.

12. The system of claim 11 further comprising a sheath surrounding said support element, wherein at least one of said filter elements is movable into said sheath in order to radially contract said at least one of said filter elements into the closed condition.

13. A method for preventing embolism and microembolism in a blood flow circuit incident to performance of a treatment at a location in a blood vessel, said method comprising:
    introducing a first filter element into the blood vessel downstream of the location so that the first filter element obturates the blood vessel;
    performing the treatment;
    introducing a second filter element into the blood vessel upstream of the location so that the second filter element obturates the blood vessel; and
    after the step of performing a treatment, bringing the first and second filter elements close to one another, radially collapsing the first and second filter elements and withdrawing the first and second filter elements from the blood vessel.

14. The method of claim 13, further comprising applying a suction between the first and second filter elements at least after the step of performing a treatment.

15. A method for performing angioplasty comprising:

aligning a first balloon with an obstruction in a blood vessel, the first balloon being radially outwardly expandable;

interposing a second balloon between the first balloon and the obstruction, the second balloon being annular and radially outwardly expandable;

expanding the first balloon to support the second balloon; and expanding the second balloon to dilate the obstruction.

16. The method of claim 15 further comprising:

before said expanding steps, aligning a stent with the obstruction; and wherein said step of expanding the second balloon is carried out to fully expand the stent.

17. The method of claim 16 wherein said step of aligning the stent includes conveying the stent to the vicinity of the obstruction while the stent is initially retained by the second balloon within the region enclosed by the second balloon, and then advancing the stent away from the region enclosed by the second balloon and into alignment with the obstruction.

18. The method of claim 16 further comprising trapping, at a location downstream of the obstruction, debris produced during dilation of the obstruction, and removing the debris from the blood vessel.

19. The method of claim 18 wherein said step of removing is carried out by applying suction upstream of the trapping location.

20. A system for performing angioplasty comprising:

a first balloon movable into alignment with an obstruction in a blood vessel, the first balloon being radially outwardly expandable;

a second balloon movable into a position where the second balloon is interposed between said first balloon and the obstruction, said second balloon being annular and radially outwardly expandable;

means coupled to said first balloon for expanding said first balloon to support the second balloon; and means coupled to said second balloon for expanding said second balloon to dilate the obstruction.

21. The system of claim 20, further comprising a radially outwardly expandable stent initially retained by the second balloon within the region enclosed by the second balloon and displaceable away from the region enclosed by the second balloon and into alignment with the obstruction.

22. A filter element for use in a blood vessel during angioplasty, said element being made of a flexible, radially compressible, radially expandable material, said element being formed to have a conical configuration when radially expanded and being composed of a plurality of circumferential, curved strips and a plurality of longitudinal struts interconnecting said strips, said strips and struts delimiting filter openings.

23. The system of claim 1 further comprising means for monitoring blood pressure in the vascular system.

\* \* \* \* \*